(12) United States Patent
Zhang et al.

(10) Patent No.: US 10,276,359 B2
(45) Date of Patent: Apr. 30, 2019

(54) ION MOBILITY SPECTROMETER

(71) Applicant: Nuctech Company Limited, Haidian District, Beijing (CN)

(72) Inventors: Qingjun Zhang, Beijing (CN); Yuanjing Li, Beijing (CN); Zhiqiang Chen, Beijing (CN); Yanchun Wang, Beijing (CN); Ziran Zhao, Beijing (CN); Xianghua Li, Beijing (CN); Qiufeng Ma, Beijing (CN); Ge Li, Beijing (CN); Biao Cao, Beijing (CN); Qi Mao, Beijing (CN); Xiang Zou, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 0 days.

(21) Appl. No.: 15/832,193

(22) Filed: Dec. 5, 2017

(65) Prior Publication Data

US 2018/0182606 A1    Jun. 28, 2018

(30) Foreign Application Priority Data

Dec. 26, 2016 (CN) .......................... 2016 1 1220290

(51) Int. Cl.
*G01N 27/62* (2006.01)
*H01J 49/16* (2006.01)
(Continued)

(52) U.S. Cl.
CPC .......... *H01J 49/168* (2013.01); *G01N 27/622* (2013.01); *H01J 49/0013* (2013.01); *H01J 49/022* (2013.01)

(58) Field of Classification Search
CPC ............... G01N 27/622; G01N 27/624; G01N 21/3504; H01J 49/168; H01J 49/004; H01J 49/0404
(Continued)

(56) References Cited

U.S. PATENT DOCUMENTS 6,639,212 B1 * 10/2003 Guevrennont ......... B01D 59/46
                                                       250/281
6,850,403 B1 *  2/2005 Gefter ...................... H01T 23/00
                                                       361/225
(Continued)

FOREIGN PATENT DOCUMENTS

CN      102945785      2/2013
CN      104392889      3/2015
(Continued)

OTHER PUBLICATIONS

Chinese Office Action for corresponding Chinese Patent Application No. 201611220290.6 dated Jan. 11, 2018, 7 pages.

*Primary Examiner* — David A Vanore
(74) *Attorney, Agent, or Firm* — Merchant & Gould P.C.

(57) ABSTRACT

The present disclosure provides an ion mobility spectrometer, which comprises: a power supply circuit, configured to provide a power supply voltage; a corona discharge configured to generate ions to be subjected to measurement, through corona discharge; an ion migration circuit configured to control migration of the ions; a migration zone structure configured to realize, under control of the ion migration circuit, mobility spectrum measurement of the ions which pass through the migration zone structure; a redundant charge extraction electrode arranged between the corona discharge structure and the migration zone structure, so that the ions which are generated by the corona discharge structure can pass therethrough to reach the migration zone structure; and a redundant charge extraction circuit, wherein
(Continued)

the redundant charge extraction electrode is connected to the ground through the redundant charge extraction circuit.

10 Claims, 5 Drawing Sheets

(51) Int. Cl.
*H01J 49/00* (2006.01)
*H01J 49/02* (2006.01)
(58) Field of Classification Search
USPC .... 250/282, 281, 287, 288, 324, 423 R, 424
See application file for complete search history.

(56) References Cited

U.S. PATENT DOCUMENTS

| | | | | |
|---|---|---|---|---|
| 2003/0230711 | A1* | 12/2003 | Guevrennont | G01N 27/624 250/287 |
| 2004/0164238 | A1* | 8/2004 | Xu | G01N 27/622 250/287 |
| 2005/0116160 | A1* | 6/2005 | Guevrennont | G01N 27/624 250/282 |
| 2008/0164409 | A1* | 7/2008 | Schultz | G01N 27/622 250/282 |
| 2009/0189070 | A1* | 7/2009 | Clemmer | G01N 27/622 250/282 |
| 2014/0299759 | A1* | 10/2014 | Allsworth | H01J 49/168 250/281 |
| 2014/0319337 | A1* | 10/2014 | Cao | G01N 27/624 250/288 |
| 2015/0188295 | A1* | 7/2015 | Zhang | H01T 19/00 250/288 |

FOREIGN PATENT DOCUMENTS

| | | |
|---|---|---|
| CN | 104835713 | 8/2015 |
| CN | 206274506 | 6/2017 |

\* cited by examiner

ION MOBILITY SPECTROMETER

CROSS-REFERENCE TO RELATED APPLICATION(S)

This application claims priority to the Chinese Patent Application No. 201611220290.6, filed on Dec. 26, 2016, which is incorporated herein by reference in its entirety.

TECHNICAL FIELD

The present disclosure relates to the field of ion spectrum measurement, and more particularly, to an ion mobility spectrometer.

BACKGROUND

Ion mobility spectrometers realize differentiation of ions according to different drift speeds of different ions in a uniform weak electric field. Ion mobility spectrometers are widely used in many fields, such as detection of drugs and explosives, due to their high differentiation speed, high sensitivity, absence of a vacuum environment and ease of miniaturization.

A typical ion mobility spectrometer usually consists of a sample injection part, an ionization part, an ion gate, a migration zone, a collection zone, a readout circuit, a data acquisition and processing part, a control part etc. The ionization part has a primary function of converting sample molecules into ions for migration and separation, and an ionization effect of the ionization part has a very direct impact on performance of the ion mobility spectrometer.

In order to achieve better ionization performance, an ion mobility spectrometer which performs ionization using corona discharge has been used. Corona discharge refers to a phenomenon in which ionization of gas molecules is caused by a local strong electric field in a spatial non-uniform electric field. Ions generated directly by corona discharge are generally referred to as reactant ions. When sample molecules with a high proton or electron affinity pass through the ionization zone, they may be ionized by trapping charges of reactant ions. A common corona discharge structure is simple and has a low cost, and may produce a high charge concentration, thereby greatly improving sensitivity and a dynamic range of the ion mobility spectrometer.

However, the high charge concentration generated by corona discharge further requires the ion mobility spectrometer to collect and process the charges more properly; otherwise it may seriously affect the stability of the device. How to achieve a more stable corona discharge based ion mobility spectrometer is one of the most urgent problems in the related art.

SUMMARY

The present disclosure proposes an ion mobility spectrometer.

According to an aspect of the present disclosure, there is proposed an ion mobility spectrometer, comprising:

a power supply circuit, configured to provide a power supply voltage;

a corona discharge structure having an input terminal connected to the power supply circuit and configured to generate ions to be subjected to measurement, through corona discharge;

an ion migration circuit coupled to the power supply circuit and configured to control migration of the ions;

a migration zone structure connected to the ion migration circuit and configured to realize, under control of the ion migration circuit, mobility spectrum measurement of the ions which pass through the migration zone structure;

a redundant charge extraction electrode arranged between the corona discharge structure and the migration zone structure, so that the ions which are generated by the corona discharge structure can pass therethrough to reach the migration zone structure; and a redundant charge extraction circuit connected to the power supply circuit, the input terminal of the corona discharge structure, the migration zone structure, and the redundant charge extraction electrode, wherein the redundant charge extraction electrode is connected to the ground through the redundant charge extraction circuit.

In an embodiment, the redundant charge extraction circuit comprises a first voltage divider, a second voltage divider and a direct current blocking capacitor, wherein the first voltage divider has one terminal connected to the power supply circuit and the input terminal of the corona discharge structure, and the other terminal connected to a first node, the second voltage divider has one terminal connected to the first node and the other terminal connected to the migration zone structure, the direct current blocking capacitor has one terminal connected to the first node and the other terminal connected to the ground, and the redundant charge extraction circuit is connected to the redundant charge extraction electrode at the first node.

In an embodiment, the corona discharge structure comprises a corona pin and a discharge tube, wherein the corona pin has one terminal serving as the input terminal of the corona discharge structure and the other terminal configured to generate the ions through discharge, and the discharge tube is arranged around the corona pin to laterally surround the other terminal of the corona pin.

In an embodiment, the redundant charge extraction circuit is further connected to the discharge tube of the corona discharge structure at a second node, and comprises a first voltage divider, a second voltage divider, a third voltage divider, a first direct current blocking capacitor and a second direct current blocking capacitor, wherein the first voltage divider has one terminal connected to the power supply circuit and the input terminal of the corona discharge structure, and the other terminal connected to the second node, the second voltage divider has one terminal connected to a first node, and the other terminal connected to the migration zone structure, the third voltage divider is connected between the first node and the second node;

the first direct current blocking capacitor has one terminal connected to the first node, and the other terminal connected to the ground, the second direct current blocking capacitor has one terminal connected to the second node, and the other terminal connected to the ground, and the redundant charge extraction circuit is connected to the redundant charge extraction electrode at the first node.

In an embodiment, the migration zone structure comprises a storage ring, an ion gate, multiple mobility field electrode plates, a suppression grid and a Faraday plate which are arranged sequentially from an input terminal to an output terminal, wherein one terminal of the storage ring, one terminal of a first mobility field electrode plate and one terminal of a last mobility field electrode plate are connected to the ion migration circuit at different nodes respectively, the other terminals of the multiple mobility field electrode plates are connected to first terminals of the multiple serially connected resistors in one-to-one correspondence, wherein a number of the multiple resistors is the same as that of the multiple mobility field electrode plates, and a last one of the multiple resistors is connected to the redundant charge extraction circuit.

In an embodiment, the ion migration circuit respectively generates different potentials at the nodes where one terminal of the storage ring, one terminal of the first mobility field electrode plate, and one terminal of the last mobility field electrode plate are connected thereto respectively.

In an embodiment, the power supply circuit comprises a power supply, a first resistor and a third direct current blocking capacitor, wherein the power supply has one terminal connected to the ion migration circuit, and the other terminal connected to one terminal of the first resistor, the first resistor has one terminal connected to the power supply, and the other terminal connected to one terminal of the third direct current blocking capacitor and the input terminal of the corona discharge circuit, and the third direct current blocking capacitor has one terminal connected to the first resistor, and the other terminal connected to the ground.

In an embodiment, the first voltage divider and the second voltage divider are resistors.

In an embodiment, the third voltage divider is a resistor or a Zener diode.

DETAILED DESCRIPTION

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known structures, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the accompanying drawings provided here are for the purpose of illustration and are not necessarily to be drawn to scale. The term "and/or" used herein means any and all combinations of one or more listed items.

The present disclosure will be described in detail below with reference to accompanying drawings.

Figure 1:
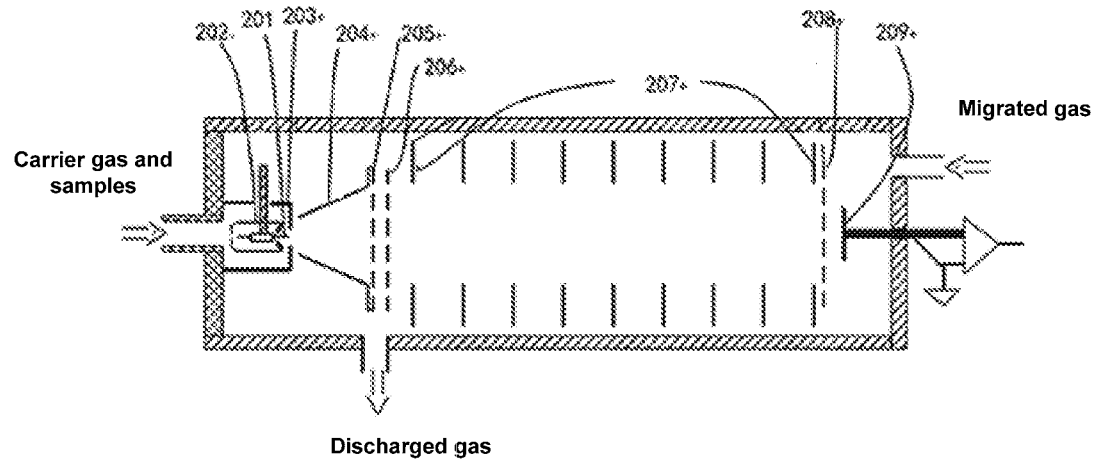
FIG. 1 illustrates a schematic diagram of a corona discharge based ion mobility spectrometer.

Firstly, FIG. 1 illustrates a schematic diagram of a corona discharge based ion mobility spectrometer. In FIG. 1, charged particles generated by discharge of a corona pin 201 are focused by a focusing electrode 202 and then enter a storage ring 204 through a corona tube 203. After that, the charged particles are injected into an ion drift zone formed by electrode plates 207 within a specific time under the control of an electric field of ion gates 205 and 206, are received by a Faraday plate 209 after being regulated by a suppression grid 208, are then converted into an electrical signal by a charge-sensitive integration and amplification circuit, and enter a signal processing system.

Figure 2:
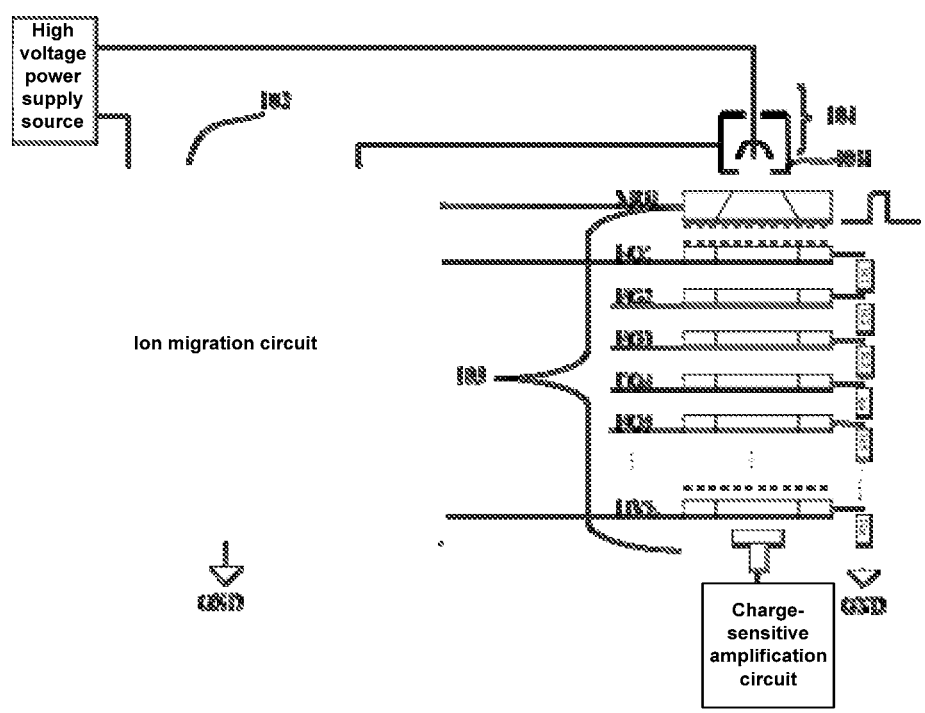
FIG. 2 illustrates a structural diagram of the corona discharge based ion mobility spectrometer illustrated in FIG. 1.
Figure 6:
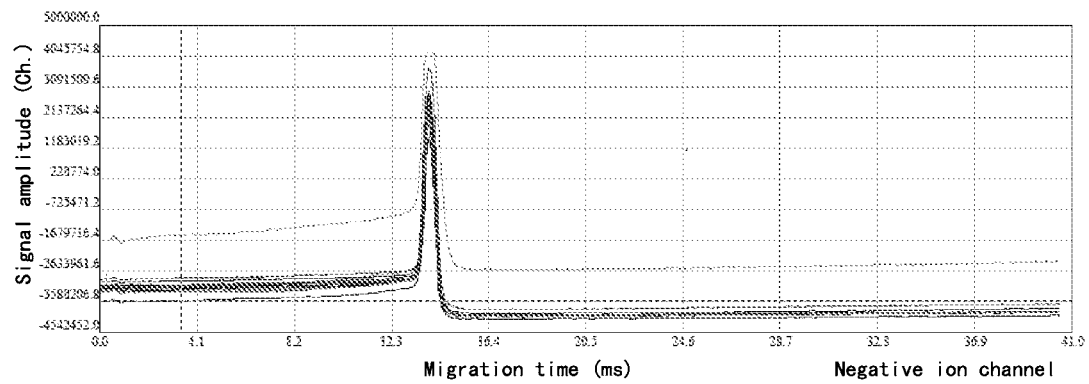
FIG. 6 illustrates a diagram of an ion mobility spectrum measured by the corona discharge based ion mobility spectrometer illustrated in FIG. 1.

FIG. 2 is a structural diagram of the corona discharge based ion mobility spectrometer in FIG. 1. In FIG. 2, charges generated by a corona discharge structure move toward the storage ring under the common control of the electric field and an air flow of injected samples. At this time, more ions may impinge on a corona discharge tube 1041 and the storage ring MG1. Both the corona discharge tube 1041 and the storage ring MG1 are directly connected to an ion migration circuit, so that the ions received by the corona discharge tube 1041 and the storage ring MG1 may enter the ion migration circuit and adversely affect the ion migration circuit, thereby affecting the stability of the ion mobility spectrum. The ion mobility spectrum measured by the ion mobility spectrometer illustrated in FIG. 1 is shown in FIG. 6.

Figure 3:
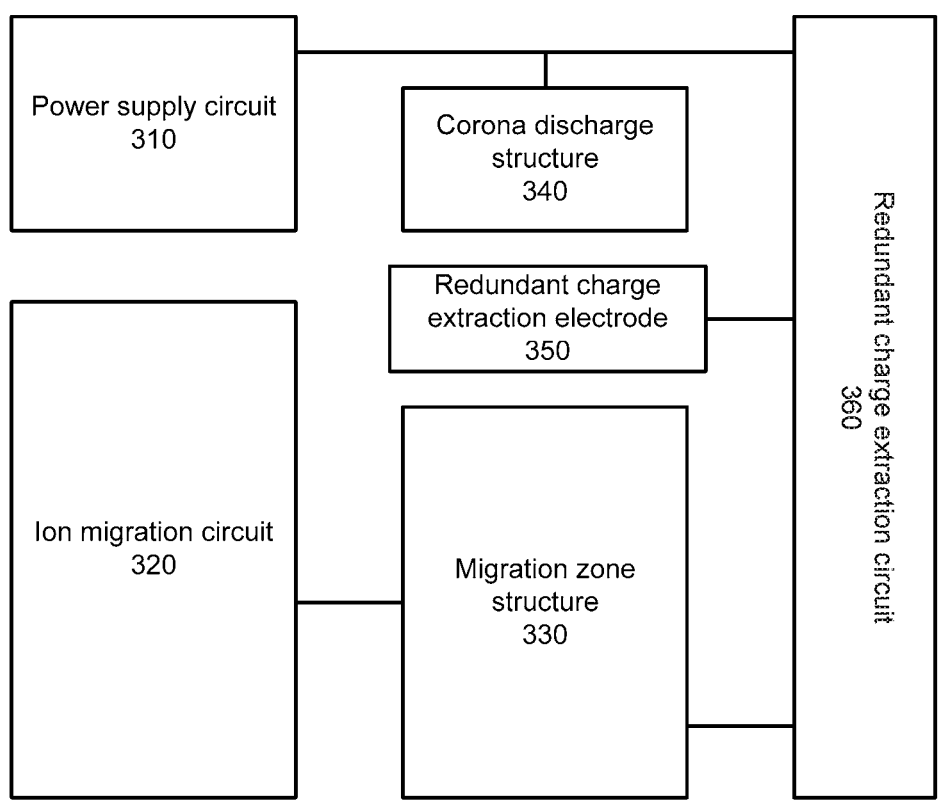
FIG. 3 illustrates a structural diagram of a corona discharge based ion mobility spectrometer according to an embodiment of the present disclosure.

FIG. 3 illustrates a structural diagram of an ion mobility spectrometer 300 according to an embodiment of the present disclosure.

As shown in FIG. 3, the ion mobility spectrometer 300 comprises a power supply circuit 310, an ion migration circuit 320, a migration zone structure 330, a corona discharge structure 340, a redundant charge extraction electrode 350 and a redundant charge extraction circuit 360. Ions generated by the corona discharge structure 340 through corona discharge successively pass through the redundant charge extraction electrode 350 (for example, in a ring shape) which has an opening in the middle and the migration zone structure 330 which forms a charge drift path, so as to realize mobility spectrum measurement of the ions which pass through the migration zone structure 330. The arrangement of the redundant charge extraction electrode 350 and the redundant charge extraction circuit 360 allows charges of the redundant ions generated through corona discharge to be absorbed so as not to affect the ion migration circuit 320.

Specifically, the power supply circuit 310 is configured to provide a power supply voltage.

The ion migration circuit 320 is connected to the power supply circuit and is configured to control migration of the ions.

The migration zone structure 330 is connected to the ion migration circuit 320 and is configured to realize, under control of the ion migration circuit 320, mobility spectrum measurement of the ions which pass through the migration zone structure 330. The corona discharge structure 340 has an input terminal connected to the power supply circuit 310 and is configured to generate ions to be subjected to measurement, through corona discharge.

The redundant charge extraction electrode 350 is arranged between the corona discharge structure 340 and the migration zone structure 330, so that the ions which are generated by the corona discharge structure 340 can pass therethrough (through an opening (for example, a ring hole) formed therein under the control of an electric field) to reach the migration zone structure 330.

The redundant charge extraction circuit 360 is connected to the power supply circuit 310, the input terminal of the corona discharge structure 340, the migration zone structure 330, and the redundant charge extraction electrode 350.

Further, the redundant charge extraction circuit 360 has a ground terminal, and the redundant charge extraction electrode 350 is connected to the ground through the redundant charge extraction circuit 360 connected thereto.

Figure 4:
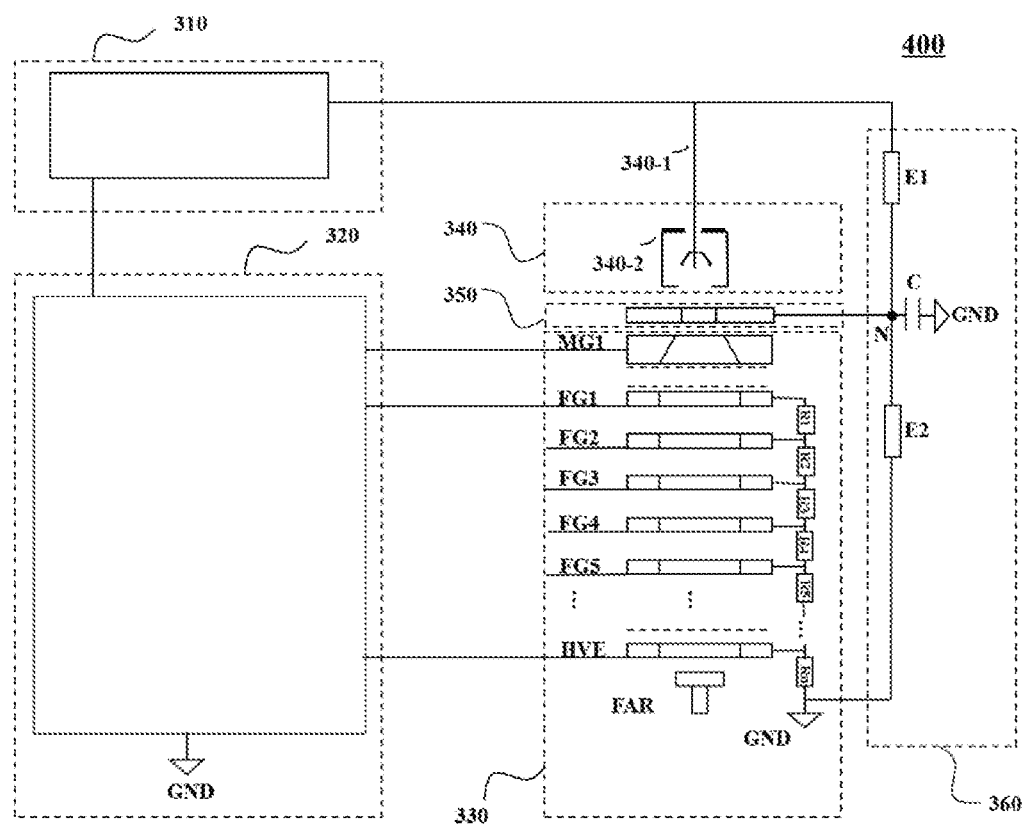
FIG. 4 illustrates a diagram of a detailed structure of the corona discharge based ion mobility spectrometer illustrated in FIG. 3.

FIG. 4 illustrates a diagram of a detailed structure 400 of the corona discharge based ion mobility spectrometer 300 illustrated in FIG. 3.

As shown in FIG. 4, the corona discharge structure 240 comprises a corona pin 340-1 and a discharge tube 340-2, wherein the corona pin 340-1 has one terminal connected to the power supply circuit 310 as the input terminal of the corona discharge structure 340 and the other terminal configured to generate the ions through discharge, and the discharge tube 340-2 is arranged around the corona pin 340-1 to laterally surround the other terminal of the corona pin 340-1.

In an embodiment, the migration zone structure 330 comprises a storage ring MG1, an ion gate, n (which is a positive integer) mobility field electrode plates FG1 to HVE, a suppression grid (not shown) and a Faraday plate FAR which are arranged sequentially from an input terminal to an output terminal (i.e., from top to bottom in the figure). One terminal of the storage ring MG1, one terminal of a first mobility field electrode plate FG1 and one terminal of a last mobility field electrode plate HVE are connected to the ion migration circuit 320 at different nodes (three connection points illustrated on the right side of the ion migration circuit 320 in FIG. 4) respectively. Other terminals of the n mobility field electrode plates are connected to first terminals of the n serially connected resistors in one-to-one correspondence. Thus, a number of the resistors is the same as that of the mobility field electrode plates. A last resistor Rn of the n resistors is connected to the redundant charge extraction circuit 360.

The ion migration circuit 320 generates different potentials at the nodes where the storage ring MG1, the first mobility field electrode plate FG1, and the last mobility field electrode plate HVE are connected thereto, respectively. Thus, according to the specific structure of the migration zone structure 330 as described above, a continuous electric field may be generated therein to direct the ions to the Faraday plate FAR.

As shown in FIG. 4, the redundant charge extraction circuit 360 comprises a first voltage divider E1, a second voltage divider E2 and a direct current blocking capacitor C.

The first voltage divider E1 has one terminal connected to the power supply circuit 310 and the input terminal of the corona discharge structure 340, and the other terminal connected to a first node N.

The second voltage divider E2 has one terminal connected to the first node N and the other terminal connected to the migration zone structure 330.

In an embodiment, the first voltage divider E1 and the second voltage divider E2 are resistors.

The first voltage divider E1 and the second voltage divider E2 are provided with specific voltage division capabilities (for example, with specific resistance values when the first voltage divider E1 and the second voltage divider E2 are resistors), so that the redundant charge extraction electrode 350 connected to the first node N has a specific potential, to enable ions generated at the corona discharge structure 340 to move downward under the control of an electric field and enter the migration zone structure 330 through the redundant charge extraction electrode 350.

In an embodiment, the voltage division capabilities of the first voltage divider E1 and the second voltage divider E2 are set, so that a potential difference between the redundant charge extraction electrode 350 and the storage ring MG1 in the migration zone structure 330 is between 60 volts and 70 volts.

The direct current blocking capacitor C has one terminal connected to the first node N, and the other terminal connected to the ground GND.

It can be seen from the figure that the redundant charge extraction circuit 360 is connected to the redundant charge extraction electrode 350 at the first node N. The redundant charge extraction electrode 350 is connected to the ground GND via the first node N and the direct current blocking capacitor C. Thereby, the charges impinging on the redundant charge extraction electrode 350 can be absorbed.

It should be noted that the specific structure illustrated in FIG. 4 is merely an exemplary illustration of the ion mobility spectrometer according to the present disclosure, and the ion mobility spectrometer according to the present disclosure is not limited to the above details. It can be understood by those skilled in the art that the influence of redundant charges on the spectrogram in the existing ion mobility spectrometer can be eliminated or suppressed by the arrangement of the redundant charge extraction electrode 350 and the redundant charge extraction circuit 360 according to the present disclosure. It can be envisioned that the arrangement of the redundant charge extraction electrode 350 and the redundant charge extraction circuit 360 according to the present disclosure can be adapted to any corona discharge based ion mobility spectrometer which is influenced by redundant charges.

In addition, the ion migration circuit 320 and the migration zone structure 330 are also shown in FIG. 4 as being connected to the ground. However, it should be understood that in other embodiments, the ion migration circuit 320 and the migration zone structure 330 may be connected to other specific potentials or may not be provided with this ground connection.

Figure 5:
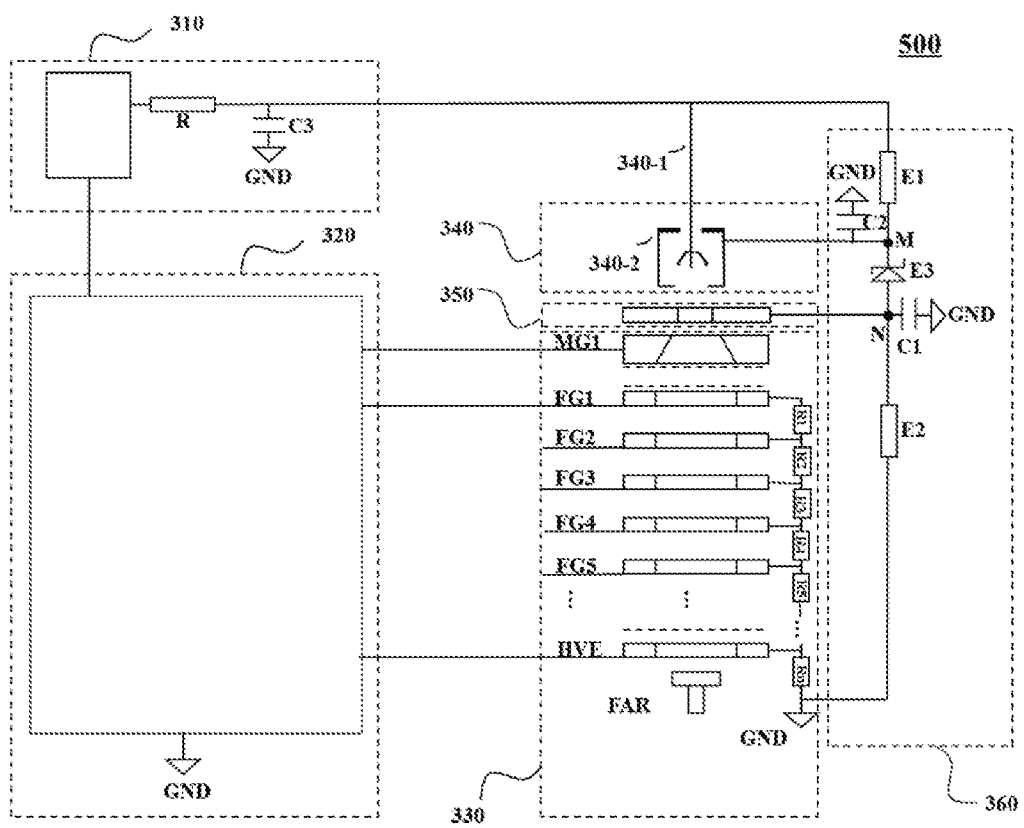
FIG. 5 illustrates a diagram of a detailed structure of the corona discharge based ion mobility spectrometer illustrated in FIG. 3.

FIG. 5 illustrates a diagram of a detailed structure 500 of the corona discharge based ion mobility spectrometer 300 illustrated in FIG. 3. The detailed structure 500 in FIG. 5 differs from the detailed structure 400 in FIG. 4 in the structures of the redundant charge extraction circuit 360 and the power supply circuit 310. It can be understood by those skilled in the art that all the improvements to the structures of the redundant charge extraction circuit 360 and the power supply circuit 310 are included in the embodiment illustrated in FIG. 5, and are merely for convenience of description. Embodiments in which only the structure of the redundant charge extraction circuit 360 or the power supply circuit 310 is improved as in FIG. 5 are also covered in the scope of the present disclosure.

The redundant charge extraction circuit 360 is shown in FIG. 5 as being connected to the discharge tube 340-2 of the corona discharge structure 340 at a second node M.

The redundant charge extraction circuit 360 comprises a first voltage divider E1, a second voltage divider E2, a third voltage divider E3, a first direct current blocking capacitor C1 and a second direct current blocking capacitor C2.

The first voltage divider E1 has one terminal connected to the power supply circuit 310 and the input terminal of the corona discharge structure 340, and the other terminal connected to the second node M.

The second voltage divider E2 has one terminal connected to the first node N, and the other terminal connected to the migration zone structure 330.

The third voltage divider E3 is connected between the first node N and the second node M. In an embodiment, the third voltage divider E3 is a resistor or a Zener diode.

The first direct current blocking capacitor C1 has one terminal connected to the first node N, and the other terminal connected to the ground GND.

The second direct current blocking capacitor C2 has one terminal connected to the second node M, and the other terminal connected to the ground GND.

Similarly, the redundant charge extraction circuit 360 is connected to the redundant charge extraction electrode 350 at the first node N.

In the structure 500 illustrated in FIG. 5, the discharge tube 340-2 of the corona discharge structure 340 is connected to the ground GND via the second direct current blocking capacitor C2, so that the redundant charges generated at the discharge tube 340-2 can also be absorbed, thereby preventing the charges accumulated thereon from affecting a potential distribution of the entire device, and better improving the performance of the device.

The first voltage divider E1, the second voltage divider E2 and the third voltage divider E3 are provided with specific voltage division capabilities (for example, with specific resistance values when the first voltage divider E1, the second voltage divider E2 and the third voltage divider E3 are resistors), so that the redundant charge extraction electrode 350 connected to the first node N and the discharge tube 340-2 connected to the second node M have specific potentials, to enable ions generated at the corona discharge structure 340 to move downward under the control of an electric field and enter the migration zone structure 330 through the redundant charge extraction electrode 350.

In an embodiment, the voltage division capabilities of the first voltage divider E1, the second voltage divider E2, and the third voltage divider E3 are set, so that a potential difference between the redundant charge extraction electrode 350 and the storage ring MG1 in the migration zone structure 330 is between 60 volts and 70 volts, and a potential difference between the discharge tube 340-2 and the redundant charge extraction electrode 350 is also between 60 volts and 70 volts. In addition, a potential difference between 2000 volts and 3000 volts may further be provided between the corona pin 340-1 and the discharge tube 340-2.

In FIG. 5, the power supply circuit 310 comprises a power supply, a first resistor R and a third direct current blocking capacitor C3. The power supply has one terminal connected to the ion migration circuit 320, and the other terminal connected to one terminal of the first resistor R. The first resistor R has one terminal connected to the power supply, and the other terminal connected to one terminal of the third direct current blocking capacitor C3 and the input terminal of the corona discharge circuit 340. The third direct current blocking capacitor C3 has one terminal connected to the first resistor R, and the other terminal connected to the ground GND. The first resistor R and the third direct current blocking capacitor C3 are arranged to enable a voltage applied by the power supply to be filtered and divided.

Figure 7:
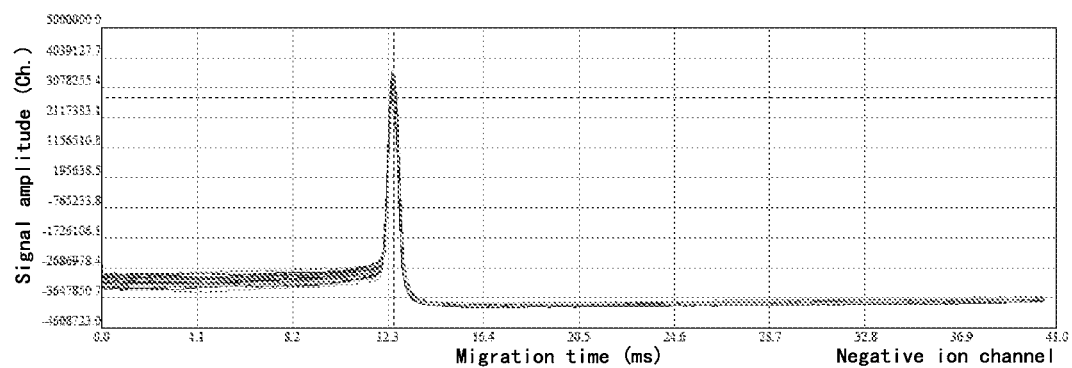
FIG. 7 illustrates a diagram of an ion mobility spectrum measured by the corona discharge based ion mobility spectrometer according to the embodiment of the present disclosure illustrated in FIG. 3.

FIG. 6 and FIG. 7 respectively illustrate a diagram of an ion mobility spectrum measured by the corona discharge based ion mobility spectrometer illustrated in FIG. 1 and a diagram of an ion mobility spectrum measured by the corona discharge based ion mobility spectrometer 300 according to the embodiment of the present disclosure illustrated in FIG. 3. It can be seen from the figure that the ion mobility spectrum measured by the ion mobility spectrometer 300 is more stable.

With the corona discharge based ion mobility spectrometer according to the present disclosure, the redundant charges which adversely affect the ion mobility spectrum can be eliminated. Thereby, the generated ion mobility spectrum is accurate and stable, thus solving the problems in the related art as described above.

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

We claim:

1. An ion mobility spectrometer, comprising:
   a power supply circuit, configured to provide a power supply voltage;
   a corona discharge structure having an input terminal connected to the power supply circuit and configured to generate, through corona discharge, ions to be subjected to measurement;
   an ion migration circuit coupled to the power supply circuit and configured to control migration of the ions;
   a migration zone structure connected to the ion migration circuit and configured to realize, under control of the ion migration circuit, mobility spectrum measurement of the ions that pass through the migration zone structure;
   a redundant charge extraction electrode arranged between the corona discharge structure and the migration zone structure, without directly connecting to the migration zone structure, so that the ions which are generated by the corona discharge structure can pass therethrough to reach the migration zone structure; and
   a redundant charge extraction circuit connected to the power supply circuit, the input terminal of the corona discharge structure and the migration zone structure, the redundant charge extraction circuit being directly connected to the redundant charge extraction electrode, wherein the redundant charge extraction electrode is connected to ground via the redundant charge extraction circuit, so that charges of ions failed to pass through the redundant charge extraction electrode can be extracted to the ground via the redundant charge extraction circuit without reaching the ion migration circuit.

2. The ion mobility spectrometer according to claim 1, wherein the redundant charge extraction circuit comprises a first voltage divider, a second voltage divider and a direct current blocking capacitor, wherein the first voltage divider has one terminal connected to the power supply circuit and the input terminal of the corona discharge structure, and the other terminal connected to a first node, the second voltage divider has one terminal connected to the first node and the other terminal connected to the migration zone structure, the direct current blocking capacitor has one terminal connected to the first node and the other terminal connected to the ground, and the redundant charge extraction circuit is connected to the redundant charge extraction electrode at the first node.

3. The ion mobility spectrometer according to claim 2, wherein the first voltage divider and the second voltage divider are resistors.

4. The ion mobility spectrometer according to claim 1, wherein the corona discharge structure comprises a corona pin and a discharge tube, wherein the corona pin has one terminal serving as the input terminal of the corona discharge structure and the other terminal configured to generate the ions through discharging, and the discharge tube is arranged around the corona pin to laterally surround the other terminal of the corona pin.

5. The ion mobility spectrometer according to claim 4, wherein the redundant charge extraction circuit is further connected to the discharge tube of the corona discharge structure at a second node, and comprises a first voltage divider, a second voltage divider, a third voltage divider, a first direct current blocking capacitor and a second direct current blocking capacitor, wherein the first voltage divider has one terminal connected to the power supply circuit and the input terminal of the corona discharge structure, and the other terminal connected to the second node, the second voltage divider has one terminal connected to a first node, and the other terminal connected to the migration zone structure, the third voltage divider is connected between the first node and the second node;

the first direct current blocking capacitor has one terminal connected to the first node, and the other terminal connected to the ground, the second direct current blocking capacitor has one terminal connected to the second node, and the other terminal connected to the ground, and the redundant charge extraction circuit is connected to the redundant charge extraction electrode at the first node.

6. The ion mobility spectrometer according to claim 5, wherein the first voltage divider and the second voltage divider are resistors.

7. The ion mobility spectrometer according to claim 5, wherein the third voltage divider is a resistor or a Zener diode.

8. The ion mobility spectrometer according to claim 1, wherein the migration zone structure comprises a storage ring, an ion gate, multiple mobility field electrode plates, a suppression grid and a Faraday plate, which are arranged sequentially from an input terminal to an output terminal, wherein one terminal of the storage ring, one terminal of a first mobility field electrode plate and one terminal of a last mobility field electrode plate are connected to the ion migration circuit at different nodes, respectively, the other terminals of the multiple mobility field electrode plates are connected to first terminals of multiple serially connected resistors in one-to-one correspondence, wherein a number of the multiple resistors is the same as that of the multiple mobility field electrode plates, and a last one of the multiple resistors is connected to the redundant charge extraction circuit.

9. The ion mobility spectrometer according to claim 8, wherein the ion migration circuit generates different potentials at the nodes where one terminal of the storage ring, one terminal of the first mobility field electrode plate, and one terminal of the last mobility field electrode plate are connected thereto, respectively.

10. The ion mobility spectrometer according to claim 1, wherein the power supply circuit comprises a power supply, a first resistor and a third direct current blocking capacitor, wherein the power supply has one terminal connected to the ion migration circuit, and the other terminal connected to one terminal of the first resistor, the first resistor has one terminal connected to the power supply, and the other terminal connected to one terminal of the third direct current blocking capacitor and the input terminal of the corona discharge circuit, and the third direct current blocking capacitor has one terminal connected to the first resistor, and the other terminal connected to the ground.

* * * * *